United States Patent [19]

Gough

[11] Patent Number: 5,523,079
[45] Date of Patent: Jun. 4, 1996

[54] HAIR STYLING COMPOSITION

[75] Inventor: Anthony D. Gough, Wirral, England

[73] Assignee: Chesebrough-Pond's USA Co., Division of Conopco, Inc., Greenwich, Conn.

[21] Appl. No.: 400,311

[22] Filed: Mar. 6, 1995

Related U.S. Application Data

[60] Continuation of Ser. No. 103,006, Aug. 5, 1993, abandoned, which is a division of Ser. No. 806,967, Dec. 12, 1991, Pat. No. 5,256,407.

[30] Foreign Application Priority Data

Dec. 13, 1990 [EP] European Pat. Off. .............. 90313607

[51] Int. Cl.$^6$ .................... A61K 7/11; A61K 7/06
[52] U.S. Cl. ...................... 424/70.11; 424/70.13
[58] Field of Search .................. 424/70.13, 70.11

[56] References Cited

U.S. PATENT DOCUMENTS

| | | | |
|---|---|---|---|
| 4,876,300 | 10/1989 | Seltzer | 524/100 |
| 4,985,239 | 1/1991 | Yanagi | 424/70 |
| 5,037,818 | 8/1991 | Sime | 514/183 |
| 5,085,857 | 2/1992 | Reid | 424/70 |
| 5,120,532 | 6/1992 | Wells | 424/70 |
| 5,143,723 | 9/1992 | Calvo | 424/63 |

FOREIGN PATENT DOCUMENTS

| | | |
|---|---|---|
| 0035901 | 9/1981 | European Pat. Off. . |
| 0240350 | 10/1987 | European Pat. Off. . |
| 0388110 | 9/1990 | European Pat. Off. . |
| 1102563 | 11/1955 | France . |
| 1579934 | 11/1980 | United Kingdom . |
| 1579935 | 11/1980 | United Kingdom . |
| 2185683 | 1/1987 | United Kingdom . |

OTHER PUBLICATIONS

"Polysynlane: a novel synthetic substitute for Squalane", Cosmetics and Toiletries, Jan. 1976; vol. 91; p. 33.
Kosmetika (Zurich), 4, pp. 84–85, (1974), P. Hoffenberg.

*Primary Examiner*—Sallie M. Gardner
*Attorney, Agent, or Firm*—Milton L. Honig

[57] ABSTRACT

A hair styling composition for imparting body and/or stylability to hair, comprises (a) at least one of surfactant, conditioning agent and water or other volatile solvent, together with (b) a per-alk(en)yl hydrocarbon material.

15 Claims, No Drawings

HAIR STYLING COMPOSITION

This is a continuation application of Ser. No. 08/103,006 filed Aug. 5, 1993, now abandoned; which is a divisional application of Ser. No. 07/806,967 filed Dec. 12, 1991 that matured into U.S. Pat. No. 5,256,407 issued Oct. 26, 1993.

BACKGROUND OF THE INVENTION

The present invention relates to hair styling compositions, in particular to such compositions which impart stylability and/or a thicker feel to hair.

When washing the hair with conventional shampoo compositions, the hair sometimes becomes less easy to comb or style. Hair conditioners and hair setting aids have been developed to try to impart more body and stylability to hair.

EP-A-240 350 discloses the use of specific silicone polymers dissolved in a volatile carrier material for giving improved style retention to hair.

There have also in the past been disclosed various oil-based cosmetic bases containing particular hydrocarbon materials, but these have only been proposed for use on the skin.

In FR-A-1102563 (published 1955) there is disclosed an elastic cosmetic fixative for hair and moustaches, consisting of an elastomer dissolved in a hydrocarbon, especially vaseline oil. The compositions exemplified are unsuitable for use as hair styling aids which impart body and a thicker feel to hair as demanded by modern trends, owing to their physical nature and excessive fixing effect on hair.

SUMMARY OF THE INVENTION

Surprisingly, it has now been found that specific adhesive and/or resinous hydrocarbon materials can be successfully formulated into hair styling compositions which impart body, a thicker feel and stylability to hair.

Accordingly, the present invention provides a hair styling composition for imparting body and/or stylability to hair, comprising (a) at least one of surfactant, conditioning agent and water or other volatile solvent, together with (b) a per-alk(en)yl hydrocarbon material.

DETAILED DESCRIPTION OF THE INVENTION

The invention will now be described in detail.

The Per-alk(en)yl Hydrocarbon Material

For the purpose of the present invention a per-alk(en)yl hydrocarbon material is a branched alk(en)yl material, of which the side-groups are —H, $C_{1-4}$ alk(en)yl groups or (—H or $C_{1-4}$ alk(en)yl) substituted saturated or unsaturated cyclic hydrocarbons, and wherein at least 10% by number of the side-groups are other than —H, more preferably from 25% to 75%, most preferably from 40% to 60%. Preferred alkyl side-groups are methyl groups.

Preferably the weight average molecular weight of the per-alk(en)yl hydrocarbon material is between 150 and 10,000,000, more preferably 160 to 1,000,000, even more preferably 170–500,000. A particularly preferred weight average molecular weight range is 2,000 to 500,000.

An especially preferred embodiment of the present invention relates to the use of per-alk(en)yl hydrocarbon materials having a relatively high molecular weight of 20,000 to 1,000,000, more preferably 20,000 to 500,000, most preferably 40,000 to 200,000; these materials are especially effective in imparting body to hair.

In another embodiment of the invention the per-alk(en)yl hydrocarbon material used has a relatively low molecular weight of 2,000 to 20,000, more preferably 5,000 to 10,000. Such low molecular weight per-alk(en)yl hydrocarbon materials are available for example from Nippon Oil and Fats under the trade name POLYSYNLANE.

In an even more preferred embodiment of the invention a per-alk(en)yl hydrocarbon material of relatively high molecular weight (as defined above) is dissolved or dispersed in a solvent or carrier. Any solvent or carrier capable of solubilizing the per-alk(en)yl hydrocarbon material may be used. Preferred are hydrocarbon solvents, e.g. low molecular weight straight or branched chain hydrocarbons, which may advantageously be short chain oligomers of the monomer from which the high molecular weight material is derived.

Thus, a particularly preferred embodiment of the invention relates to the combined use of per-alk(en)yl hydrocarbon materials of relatively high molecular weight (as defined above) with per-alk(en)yl hydrocarbon materials of low molecular weight (for example 70–5,000, more preferably 150–2,000, most preferably 150–500), whereby the high molecular weight materials are mainly effective for imparting body to hair, while the low molecular weight materials aid even dispersion in the hair styling composition and even deposition of the materials on the hair.

Preferably the weight ratio between high molecular weight per-alk(en)yl hydrocarbon materials and low molecular weight per-alk(en)yl hydrocarbon materials is from 10:1 to 1:10, most preferably 2:1 to 1:5. Preferably the high molecular weight material is soluble in the low molecular weight material.

Preferred per-alk(en)yl hydrocarbon materials are polymers of butene, isoprene, terpene and styrene, and copolymers of any combination of these monomers, such as butyl rubber (poly isobutylene-co-isoprene), natural rubber (cis-1,4-polyisoprene) and hydrocarbon resins such as mentioned in the Encyclopedia of Chemical Technology by Kirk & Ohmer (3rd edition vol 8, pp 852–869), for example aliphatic and aromatic petroleum resins, terpene resins etc. Especially preferred is the use of polymers which are soluble in the low molecular weight per-alk(en)yl hydrocarbon material or other solvent or carrier, if used.

Especially preferred are per-alk(en)yl hydrocarbon materials of the formula:

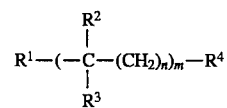

wherein:

n=0–3, preferably 1;

m=an integer such that the weight average molecular weight of the hydrocarbon will range from 2,000 to 1,000,000

$R^1$ is —H or a $C_{1-4}$ alkyl group; preferably methyl;

$R^2$ is a $C_{1-4}$ alkyl group; preferably methyl;

$R^3$ is —H or a $C_{1-4}$ alkyl group; preferably —H or methyl

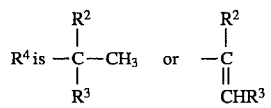

Especially preferred are polyisobutylene materials of the formula:

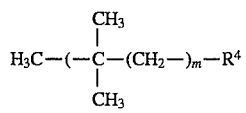

wherein $R^4$ is

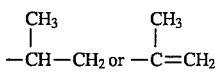

These materials are available from Presperse Inc. under the Permethyl trade name.

The total level of per-alk(en)yl hydrocarbon material in the hair styling composition is preferably from 0.01–20%, more preferably from 0.1–10%, even more preferably from 0.2 to 5%, most preferably from 0.5 to 2% by weight of the composition.

The Hair Styling Composition

Hair styling compositions in accordance with the invention contain, in addition to the per-alk(en)yl hydrocarbon material, at least one of the following components: surfactant, hair conditioning agent and water or other volatile solvent. The compositions of the invention may therefore have a similar basic formulation and/or physical nature to conventional hair styling products not containing the per-alk(en)yl hydrocarbon material and may thus be used in similar protocols.

For example, the hair styling compositions of the invention can take the form of styling sprays, mousses, lotions, conditioners and shampoos. Preferred hair styling compositions in accordance with the invention are shampoos and conditioners.

Preferred hair styling compositions of the invention comprise one or more surfactant materials.

Shampoo compositions in accordance with the present invention comprise one or more surfactants selected from anionic, nonionic, amphoteric, zwitterionic and cationic surfactants and mixtures thereof.

Suitable anionic surfactants are the alkyl sulphates, alkyl ether sulphates, alkaryl sulphonates, alkyl succinanes, alkyl sulphcsuccinates, N-alkoyl sarccsinates, alkyl phosphates, alkyl ether phosphates, alkyl ether carboxylates, and α-olefin sulphonates, especially their sodium, magnesium, ammonium and mono-, di- and tri-ethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Examples of further suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1 EO, 2 EO and 3 EO, ammonium lauryl sulphate and ammonium lauryl ether sulphate 1 EO, 2 EO and 3 EO.

The nonionic surfactants suitable for use in the composition of the invention may include condensation products of aliphatic ($C_8$–$C_{18}$) primary or secondary linear or branched-chain alcohols or phenols with alkylene oxides, usually ethylene oxide and generally 6–30 EO groups.

Other suitable nonionics include mono- or di-alkyl alkanolamides or alkyl polyglucosides. Examples include coco mono- or di-ethanolamide, coco mono-isopropanolamide, and coco di-glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alky amidopropyl hydroxysultaines, acyl taurates and acyl glutamates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

Examples of cationic surfactants include: quaternary ammonium hydroxides and salts thereof, for example cetyl trimethylammonium chloride, stearyl dimethylbenzyl ammonium chloride, cetylpyridinium chloride, quaternium-5, -31, -18 and mixtures thereof.

The level of surfactant materials, if present, in compositions of the invention is preferably more than 1%, more preferably 2–35% and most preferably from 5 to 30% by weight of the composition.

Hair styling compositions in accordance with the invention may comprise one or more hair conditioning agents.

Preferably, the amount of conditioning agent used is sufficient to impart overall hair conditioning properties to the composition when used on hair, so that such a composition provides hair conditioning and styling benefits simultaneously. However, a minor amount of conditioning agent may still advantageously be used, since although not being sufficient to render the composition a true conditioner, it is believed to ameliorate to some extent certain aspects of the bodying effect of the per-alk(en)yl hydrocarbon material, such that the resulting overall styling and/or bodying and/or thicker feel effect of the composition is superior to that obtainable using the per-alk(en)yl hydrocarbon material alone.

Suitable conditioning agents are the cationic surfactants mentioned above, which may be present in an amount of from 0.01 to 10%, preferably 0.05 to 5%, most preferably 0.1 to 2% by weight of the composition.

Alternative or additional conditioning agents include cationic polymers, volatile or non-volatile silicones, quarternized silicones (e.g. those materials available under the trade name ABILQUAT ex T. H. Goldsmith perfluoropolyethers (e.g. those materials available under the trade name FOMBLIN ex Montefluos), protein hydrolysates and quaternised protein hydrolysates.

Suitable cationic polymers include Guar Hydroxypropyltrimonium chloride, Quaternium-19, -23, -40, -57, poly (dimethyldiallylammonium chloride), poly (dimethyl butenyl ammonium chloride)-,w- bis (triethanolammonium chloride), Poly (dipropyldiallylammonium chloride), Poly (methyl-beta-propaniodiallylammonium chloride), Poly (diallylpiperidinium chloride), poly (vinyl pyridinium chloride), quaternised poly (vinyl alcohol), quaternised poly (dimethylaminoethylmethacrylate) and mixtures thereof.

Examples of suitable volatile silicone materials include those available commercially from Dow Corning as 244, 245, 344, 345 and 200 fluids (cyclopolymethylsiloxane blends), 200/5 fluid ( a very short linear polydimethylsiloxane) and 1401 fluid (a mixture of polydimethylsiloxanol gum and cyclopolymethylsiloxanes); from Union Carbide as TP503 fluid (an emulsion of polydimethylsiloxane gum in cyclopolymethylsiloxane) and Silicone 7202 and 7158; and from Stauffer Chemical as SWS-03314.

Suitable protein derivatives include lauryl dimonium hydroxy propylamino hydrolysed animal protein, available commercially under the tradename LAMEQUAT L, and hydrolysed keratin containing sulphur-bearing amino acids, available commercially under the tradename CROQUAT WKP.

Conditioning agents which are especially suitable for use in compositions according to the invention include volatile or non-volatile silicone oils, such as for example polyalkylsiloxanes, polyalkylaryl siloxanes, silicone gums, cyclomethicones and aminofunctional silicones. Preferably these silicone materials are incorporated in the compositions as small particles, preferably of particle size 0.01 to 10 microns.

The preferred level of the alternative or additional conditioning agents, if present, in compositions of the invention is up to 20%, for example from 0.01 to 10%, more preferably from 0.1 to 5% by weight Another ingredient that may advantageously be incorporated into the hair styling compositions of the invention is a fatty alcohol material. The use of such a material is especially preferred in conditioning compositions, in particular conditioning compositions which comprise one or more cationic surfactant materials. The combined use of fatty alcohol material and cationic surfactant in conditioning compositions is believed to be especially advantageous, because this leads to the formation of a lamellar phase, wherein the cationic surfactant is dispersed.

Preferred fatty alcohols contain from 8 to 22 carbon atoms, more preferably 16 to 20. Examples of preferred fatty alcohols are cetyl alcohol and stearyl alcohol. The use of these materials is also advantageous in that they contribute to the overall conditioning properties of compositions of the invention.

The level of fatty alcohol material is conveniently from 0 to 10%, more preferably from 0.1 to 5% by weight of the composition. The weight ratio of cationic surfactant to fatty alcohol may preferably be from 10:1 to 1:10, more preferably from 4:1 to 1:8, most preferably from 1:1 to 1:4.

Other Ingredients

The hair styling compositions of the invention may also include minor amounts of other ingredients commonly found in hair styling compositions, such as antibacterial agents, antidandruff agents such as zinc pyridinethione or Octopirox, foam boosters, pearlescers, perfumes, dyes, colouring agents, preservatives, viscosity modifiers, proteins, polymers, buffering agents, polyols and other moisturising agents, herb extracts, mink oil or honey.

An especially preferred ingredient for use in hair styling compositions of the invention is a deposition aid for the per-alk(en)yl hydrocarbon material. Any material capable of aiding the deposition thereof onto the hair may be used.

Conveniently the deposition aid is a cationic polymeric material. A preferred deposition polymer is a cationic derivative of guar gum, for example as available under the Jaguar trade name ex Meyhall.

Suitable cationic guar gum derivatives are those given the CTFA designation guar hydroxypropyl trimonium chloride, available commercially for example as JAGUAR C13S, which has a low degree of substitution of the cationic groups and a high viscosity. Other suitable materials include that known as JAGUAR C15, having a moderate degree of substitution and a low viscosity, JAGUAR C17 (high degree of substitution, high viscosity) and JAGUAR C16 which is a hydroxypropylated cationic guar derivative containing a low level of substituent groups as well as cationic quaternary ammonium groups. Also suitable is JAGUAR 162 which is a high transparency, medium viscosity guar having a low degree of substitution. Especially preferred is the use of Jaguar C13S.

The level of deposition aid is preferably from 0.001 to 10%, more preferably 0.01 to 5%, most preferably 0.05 to 2% by weight of the composition.

Water

Compositions of the invention preferably comprise from 20–99.5% of water, more preferably 30–90%, most preferably 40–70% by weight.

Other volatile solvents commonly used in known hair styling products may be used instead of or in addition to water, for example lower alcohols (e.g. ethanol).

Use of the Composition

After preparation, hair styling compositions according to the invention are preferably packed. Any suitable container can be used for this purpose, but generally compositions of the invention will be packed in closed containers like bottles, sachets and the like.

Hair styling compositions of the invention are generally applied in an amount of from 1 to 50 mls. Preferred amounts for shampoos are 3 to 5 mls to wet hair. After applying the shampoo the wet hair is worked to create a lather. The lather may be retained on the head for a short time before rinsing, e.g. from 1 to 4 minutes, or may immediately be rinsed. The treatment may be repeated, if required. For conditioners the preferred dosage is from 3 to 20 mls which is applied to hair after washing or rinsing, whereafter the wet hair is worked and rinsed.

The invention will be illustrated by means of the following examples:

EXAMPLE 1

A shampoo composition was made by first making a pre emulsion as indicated below by high shear stirring the mixture with a Silverson high shear mixer for 2 minutes.

| Pre-emulsion INGREDIENT (wt %) | |
|---|---|
| Sodium Lauryl 2EO sulphate | 16 |
| Tegobetain L7 | 2 |
| 70/30 mixture of Permethyl 99A/Permethyl 108A | 6.6 |
| Jaguar C13S | 0.1 |
| Water | balance |

The final shampoo was then made by mixing the pre-emulsion with the other ingredients as follows:

| INGREDIENT (wt %) | |
| --- | --- |
| Pre-emulsion | 50 |
| Sodium Lauryl 2EO sulphate | 4 |
| Tegobetain L7 | 1 |
| DNP conc E | 20 |
| Jaguar C13S | 0.05 |
| NaCl | 7 |
| Perfume | 0.4 |
| Water | balance |

The final formulation was:

| INGREDIENT (wt %) | |
| --- | --- |
| Sodium Lauryl 2EO sulchate | 12 |
| Tegobetain L7[1] | 2 |
| Jaguar C13S[2] | 0.1 |
| Permethyl 99A[3] | 2.3 |
| Permethyl 108A[4] | 1.0 |
| DNP Conc E[5] | 20 |
| Perfume | 0.4 |
| NaCl | 7 |
| water | balance |

Notes:
[1] Cocoamidopropylbetaine ex Th. Goldschmidt AG
[2] Cationic polysaccharide ex Meyhall
[3] volatile branched hydrocarbon (isododecane) ex Presperse Inc (mwt 170)
[4] high molecular weight polyisobutylene ex Presperse Inc (mwt about 50,000).
[5] Mixture of 21.4% Sodium Lauryl 2EO sulphate, 9% ethylene glycol distearate, 1,5% ethylene glycol monostearate, 8.6% coconut monoethanolamide and 0.1% NaCl in water, ex Dainihon Kasei.

Test of Permethyl 108A containing shampoo against a control

The hair body imparting ability of the shampoo above was tested in action using hair switches as follows.

Six 11.4 cm/4.5 g hair switches were prepared from Yugoslavian red tie hair ex Raoul. The switches were labelled numbers 1 to 6 and switches 1–3 were treated with the shampoo above and 4–6 were treated with a control shampoo of identical formulation but without any Permethyl 108A, according to the following protocol.

1) 0.25 g shampoo applied per switch.
2) Rubbed in by hand for 30 seconds.
3) Left on for 20 seconds.
4) Rinsed under 40° C. tap water for 30 seconds.
5) Another 0.25 g shampoo applied per switch
6) Rubbed in by hand for 30 seconds.
7) Left on for 30 seconds.
8) Rinsed under 40° C. tap water for 30 seconds.

All the switches were then set onto 30 mm diameter PTFE rollers and left to dry in a circulatory oven at 50° C. for 1 hour. The switches were then carefully removed from the rollers, allowed to cool to ambient temperature for 15 minutes and then tested for body by a trained panel of assessors using a paired comparson technique.

Twelve assessors were used and each panelist was presented with a total of six different permutations of pairs, each pair comprising a switch treated with the Permethyl 108A shampoo and a switch treated with the control shampoo.

Results

Out of the 72 paired comparisons the switch treated with the shampoo containing 108A was chosen 57 times. This is statistically significant at less than the 1% level. Thus the switches treated with the Presperse 108A shampoo were perceived to have more body than those that were treated with the control shampoo.

EXAMPLE 2

The following hair conditioner composition was prepared according to the method stated below:

| INGREDIENT (wt %) | |
| --- | --- |
| a. Cetyltrimethylammoniumchloride | 0.7 (50% soln) |
| b. 70/30 mixture of Permethyl 99A/Permethyl 108A | 2.0 |
| c. Cetostearyl alcohol | 2.3 |
| d. Glycerol monostearate | 0.7 |
| e. P-Hydroxybenzoate | 0.2 |
| f. Perfume | 0.2 |
| g. Dye | 0.0015 |
| h. Hydrochloric acid (10%) | 0.12 |
| i. Water to | 100% |

Ingredients a–c user heated together with stirring at 60° C. This mixture was then dispersed in water at 80° C. with stirring. The remaining ingredients were then added with stirring for a further 5 minutes. The mixture then allowed to cool slowly to ambient temperature.

EXAMPLE 3

A hair conditioning composition was made by first making a pre-emulsion as indicated below by mixing the ingredients in a Ystral mixer.

| Pre-emulsion INGREDIENT (weight) | |
| --- | --- |
| Sodium lauryl ether sulphate 2EO | 2.3 g |
| 70/30 mixture of Permethyl 99A/Vistanex LMMH[1] | 12 g |
| Glycerol | 20 g |

The final conditioning composition was then made by mixing the pre-emulsion with the remaining ingredients using the Ystral mixer as follows:

| INGREDIENT (weight) | |
| --- | --- |
| Pre-emulsion | 22.9 g |
| Natrosol 250HR[2] | 3.0 g |
| Arquad 16/50[3] | 2.8 g |
| Laurex CS[4] | 2.0 g |
| Water balance to | 200 g |

Notes:
[1] high molecular weight polyisobutylene ex Exxon (mwt about 50,000)
[2] hydroxyethylcellulose ex Hercules
[3] 50% cetyltrimethylammonium chloride ex Akzo
[4] cetostearyl alcohol ex Albright and Wilson
The final formulation had a polyisobutylene content of 1.2% wt.

Test of polyisobutylene-containing conditioner against a control

The hair body imparting ability of the above conditioning composition was tested as follows.

In accordance with the test procedure in Example 1, an in vitro paired comparison body test was used to compare hair switches treated with the polyisobutylene-containing conditioner against those treated with an equivalent conditioning composition not containing polyisobutylene.

The hair switches were first washed with Timotei (trade mark) shampoo and then treated with 0.5 g of conditioner. The conditioner was left on for 1 minute and then the switches were rinsed for 30 seconds, thus mimicking in-use protocol.

The voting split showed that out of 72 comparisons, the polyisobutylene-treated switches were considered to have greater body 61 times. This is statistically significant, with >99% confidence.

Ease of Wet Combing

The test used measures the total time required to comb out the tangles in wet hair switches. This is the TCT value (Total Combing Time).

Four switches were washed with Timotei shampoo (a non-conditioning product) and the TCT was recorded. They were then treated with the polyisobutylene-containing conditioner and the TCT recorded. The process was repeated with the conditioner without polyisobutylene.

The polyisobutylene-containing conditioner had an average TCT value of 59% less than that of Timotei shampoo.

The non-polyisobutylene-containing conditioner had an average TCT value of 65% less than that of Timotei shampoo.

Thus, the polyisobutylene-containing conditioner gave body whilst still providing a wet combing benefit.

I claim:

1. A hair styling composition for imparting body and/or stylability to hair comprising:
   (a) from 1 to 35% by weight of a surfactant;
   (b) from 0.1 to 5% of a per-alk(en)yl hydrocarbon material of weight average molecular weight ranging from 170 to 500,000 which is a polymer or copolymer formed from monomers selected from the group consisting of butane, isoprene and combinations thereof; and
   (c) from about 0.01 to 5% of guar hydroxypropyltrimonium chloride.

2. A composition according to claim 1, wherein the per-alk(en)yl hydrocarbon material has a weight average molecular weight in the range from 5,000 to 500,000.

3. A composition according to claim 1, wherein the per-alk(en)yl hydrocarbon material is a polybutene.

4. A hair styling composition for imparting body and/or stylability to hair comprising:
   (a) from 1 to 35% by weight of a surfactant;
   (b) from 0.1 to 5% of a per-alk(en)yl hydrocarbon material of weight average molecular weight ranging from 170 to 500,000 which is a polymer or copolymer formed from monomers selected from the group consisting of butane isoprene and combinations thereof;
   (c) from about 0.01 to 5% of guar hydroxypropyltrimonium chloride; and
   (d) an effective amount of ethylene glycol distearate sufficient to function as a pearlascar.

5. A composition according to claim 4, wherein the per-alk(en)yl hydrocarbon material has a weight average molecular weight in the range from 5,000 to 500,000.

6. A composition according to claim 4, wherein the per-alk(en)yl hydrocarbon material is a polybutene.

7. A method of imparting body and/or stylability to hair comprising applying to the hair a composition comprising:
   (a) from 1 to 35% by weight of a surfactant;
   (b) from 0.1 to 5% of a per-alk(en)yl hydrocarbon material of weight average molecular weight ranging from 170 to 500,000 which is a polymer or copolymer formed from monomers selected from the group consisting of butane, isoprene and combinations thereof; and
   (c) from about 0.01 to 5% of guar hydroxypropyltrimonium chloride.

8. A method of imparting body and/or stylability to hair comprising applying to the hair a composition comprising:
   (a) from 1 to 35% by weight of a surfactant;
   (b) from 0.1 to 5% of a per-alk(en)yl hydrocarbon material of weight average molecular weight ranging from 170 to 500,000 which is a polymer or copolymer formed from monomers selected from the group consisting of butane, isoprene and combinations thereof;
   (c) from about 0.0.1 to 5% of guar hydroxypropyltrimonium chloride; and
   (d) an effective amount of ethylene glycol distearate sufficient to function as a pearlsscar.

9. A composition according to claim 4 wherein ethylene glycol distearate is present at 1.8%.

10. A method according to claim 8 wherein ethylene glycol distearate is present at 1.8%.

11. A hair styling composition for imparting body and/or stylability to hair comprising:
    (a) from 1 to 35% by weight of an anionic or nonionic surfactant;
    (b) from 0.1 to 5% of a per-alk(en)yl hydrocarbon material of weight average molecular weight ranging from 170 to 500,000 which is a polymer or copolymer formed from monomers selected from the group consisting of butene, isoprene and combinations thereof;
    (c) from 0.01 to 5% of guar hydroxypropyltrimonium chloride; and
    (d) from 0.01 to 10% of a cationic surfactant.

12. A composition according to claim 11 further comprising a fatty alcohol containing from 8 to 22 carbon atoms, the weight ratio of cationic surfactant to fatty alcohol ranging from 10:1 to 1:10.

13. A composition according to claim 12 wherein the fatty alcohol is selected from the group consisting of cetyl alcohol, stearyl alcohol and mixtures thereof.

14. A composition according to claim 11 wherein the surfactant under (a) is an anionic surfactant selected from the group consisting of sodium lauryl sulphate, triethanolamine lauryl sulphate, triethanolamine monolauryl phosphate, sodium lauryl ether sulphate, ammonium lauryl sulphate and ammonium lauryl ether sulphate.

15. A composition according to claim 1 wherein the guar hydroxypropyltrimonium chloride is present in an amount from about 0.05 to 2% by weight.

* * * * *

UNITED STATES PATENT AND TRADEMARK OFFICE
CERTIFICATE OF CORRECTION

PATENT NO. : 5,523,079
DATED : June 4, 1996
INVENTOR(S) : Gough

It is certified that error appears in the above-indentified patent and that said Letters Patent is hereby corrected as shown below:

| | | |
|---|---|---|
| col. 9, Claim 1, | line 8, change "butane" to -- butene --. | |
| col. 9, Claim 4, | line 8, change "butane" to -- butene --; and line 12, change "pearlascar" to -- pearlescer --. | |
| col. 10, Claim 7, | line 8, change "butane" to -- butene --. | |
| col. 10, Claim 8, | line 8, change "butane" to -- butene --; and line 12, change "pearlsscar" to -- pearlescer --. | |

Signed and Sealed this

Fifteenth Day of October, 1996

BRUCE LEHMAN

Attest:

*Attesting Officer*  *Commissioner of Patents and Trademarks*